United States Patent [19]

Dahlmann et al.

[11] Patent Number: 4,945,766
[45] Date of Patent: Aug. 7, 1990

[54] METHOD AND APPARATUS FOR ULTRASONIC INSPECTION

[75] Inventors: Virgil R. Dahlmann, Bloomfield Hills; Karen M. Pirrallo; Kelly A. Talaki, both of Troy; Kenneth J. Zielesch, Fraser, all of Mich.; Robert Hickling, Oxford, Miss.

[73] Assignee: General Motors Corporation, Detroit, Mich.

[21] Appl. No.: 404,469

[22] Filed: Sep. 8, 1989

[51] Int. Cl.$^5$ ............................................. G01M 15/00
[52] U.S. Cl. .................................... 73/598; 73/119 R; 382/8
[58] Field of Search ...................... 73/119 R, 597, 598, 73/865.8, 629, 620, 598; 382/8; 367/104; 358/96

[56] References Cited

U.S. PATENT DOCUMENTS

| | | |
|---|---|---|
| 3,380,293 | 4/1968 | Murphy . |
| 3,792,423 | 2/1974 | Becker et al. . |
| 4,332,016 | 5/1982 | Berntsen ................................. 367/7 |
| 4,399,554 | 8/1983 | Perkins, III et al. .................... 382/8 |
| 4,543,659 | 9/1985 | Ozaki ....................................... 382/8 |
| 4,554,834 | 11/1985 | Prinz et al. ............................ 73/597 |
| 4,696,047 | 9/1987 | Christian et al. ........................ 382/8 |
| 4,703,440 | 10/1987 | Birk et al. ............................ 364/521 |

Primary Examiner—Jerry W. Myracle
Attorney, Agent, or Firm—Robert M. Sigler

[57] ABSTRACT

Valve spring assemblies are checked for proper assembly of keys by ultrasonically scanning a plurality of assemblies along a path crossing the stem, keys and cap to acquire profile data; compensating for temperature effects by determining the average time of flight to the stems, which are nominally the same distance from the ultrasonic sensor, and searching for each individual stem in a window centered on the average time of flight; then defining windows for the keys and cap offset from the measured surface of each stem; and searching the data for points within the respective windows to determine proper positioning of each element. The apparatus includes ultrasonic equipment, a scanning manipulator to move the ultrasonic sensor over the part, and a computer interfaced to the ultrasonic equipment and manipulator for control and data analysis.

15 Claims, 3 Drawing Sheets

METHOD AND APPARATUS FOR ULTRASONIC INSPECTION

FIELD OF THE INVENTION

This invention relates to ultrasonic inspection of object configuration and particularly to a method and apparatus for inspection of valve spring assemblies.

BACKGROUND OF THE INVENTION

Valve spring assemblies for automotive engines comprise a valve having a long stem with an annular groove near the end, a coil spring around the stem, a cap over the end of the spring, and a pair of semi-annular keys which seat in the groove and hold the cap against the spring while the cap, in turn, presses the keys into the groove by way of a tapered surface. These assemblies are put together by automatic equipment and then inspected for proper fit. To accomplish key insertion, the spring must be compressed so that the keys can lock into the valve stem groove. When the spring is released, the keys hold the spring in place. If one key should pop out or jam in a position other than in the notch, the other key will temporarily hold the assembly together, but will release when the valve is exercised. The inspection must detect any missing key to avoid that problem. Even if a key is not missing, it may not be seated properly. Thus a high key is a symptom of improper seating and must be detected.

Automatic inspection of the valve spring assemblies has been done by a machine vision system as shown in the U.S. Pat. No. 4,399,554 to Perkins III et al wherein a camera positioned above the engine can view the valve assembly and the scene is analyzed by a computer program to locate the stem and the keys surrounding the stem. A missing key is readily detected. The vision system is not sensitive to small variations in range or key height so that in practice another camera is positioned to capture a side view of the keys (which normally extend above the cap) and detect improper key height. However, some valve assemblies have the keys recessed in the cap so that the side camera can not see the keys to verify the height. Also dual contact probes coupled to LVDTs and mounted on a robot end effector are in use to make a differential measurement between the top surfaces of the stem and keys. These probes are unable to detect a missing or low key if the other key is in the stem groove.

It is thus proposed to use a sensing system which is sensitive to key height as well as to key presence so that the entire inspection can be carried out by a single sensor above the valve assembly. Ultrasonic inspection is proposed since it is based on range measurements. As shown in U.S. Pat. No. 4,554,834 to Prinz et al, an ultrasonic transducer carried by a robot can be used to map the profile of a workpiece using a focused sonic beam. Also, U.S. Pat. No. 4,332,016 to Berntsen uses ultrasonic measurements to determine characteristic three dimensional dimensions of objects which are carried past the measuring device. While it is known that ultrasonic measurements are subject to temperature effects due to the temperature dependence of the speed of sound, these patents do not reveal how to make accurate measurements in an environment where temperature may vary.

SUMMARY OF THE INVENTION

It is therefore an object of the invention to provide an ultrasonic measuring method for scanning the surface of an object to determine proper positioning of the object surfaces and particularly to such a method which automatically compensates for temperature effects.

It is another object to provide an apparatus for carrying out such a method.

The invention is carried out in an ultrasonic sensing system having a sensor for inspecting a series of objects each having a plurality of surfaces facing the sensor including a reference surface at a known nominal distance from the sensor, the method comprising the steps of: scanning the sensor over the surfaces of the objects and recording the time of flight of the ultrasonic signals, determining the average time of flight to the reference surfaces in the course of inspecting a series of objects, for each object, establishing parameters on the desired distance of each surface from the reference surface, extracting features from the recorded time of flight data, locating the feature corresponding to the reference surface based on the average time of flight and determining the reference time of flight, setting a window in which each acceptable surface other than the reference surface is to be found, and determining whether each feature for a respective surface is in a corresponding window.

The invention is further carried out by apparatus for ultrasonic inspection of object configurations where each object has a reference surface and feature surfaces to be measured, comprising: ultrasonic sensor means for emitting a series of pulses toward a surface to be measured, receiving reflected pulses and measuring the time of flight of the pulses, means for scanning the sensor means across the object in a predetermined path along the surfaces to be measured, memory means for storing the size of each surface along the scan path and the desired offset distance of each feature surface from the reference surface, and computer means including the memory means for (a) determining a reference time of flight based on a running average of pulses to the reference surfaces, (b) setting a time window based on the reference time of flight for an acceptable reference surface, (c) locating the reference surface within the said time window, d) setting a time window for each feature surface referenced to the time of flight for the located reference, and (e) comparing the time of flight for each measured object surface to the corresponding feature time window to determine acceptability.

BRIEF DESCRIPTION OF THE DRAWINGS

The above and other advantages of the invention will become more apparent from the following description taken in conjunction with the accompanying drawings wherein like references refer to like parts and wherein.

DESCRIPTION OF THE PREFERRED EMBODIMENT

The ensuing description is for a method and apparatus specifically developed for inspecting valve spring assemblies. It will be seen, however, that the application is not limited to that usage but other objects may be inspected in the same manner. In particular, a scheme of nullifying temperature effects on the ultrasonic measurements can be appropriately used elsewhere.

Figure 1:
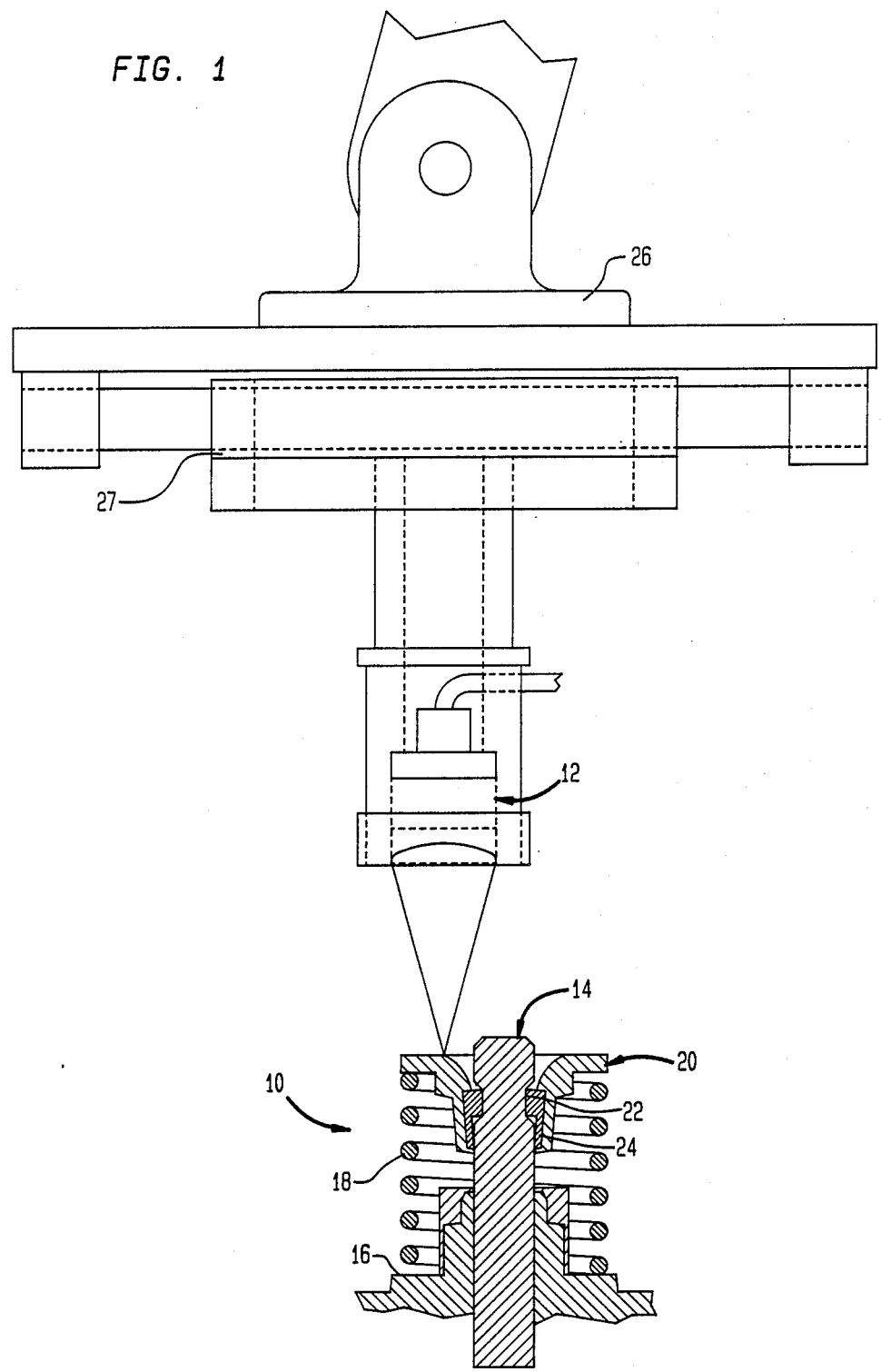
FIG. 1 is a cross sectional view of a valve spring assembly and a sensor for inspecting the assembly.

FIG. 1 shows a cross section of a valve spring assembly 10 and an ultrasonic sensor 12 above the assembly. The assembly 10 comprises a valve stem 14 protruding from an engine head 16. A coil spring 18 is compressed between the head 16 and a valve cap 20. The stem 14 has an annular groove 22 and a pair of semi-annular valve keys 24 mating with the stem 14 have internal surfaces shaped to conform to the stem and the groove 22. The keys 24 have tapered outer surfaces and the cap 20 has a tapered inner surface so that when properly assembled the spring-biased cap 22 urges the keys 24 into locking engagement with the stem 14. If the keys are not properly assembled, one key may be absent, or one key may be higher than the other. A side effect of having a high key is that the cap 20 may be tilted.

Figure 2:
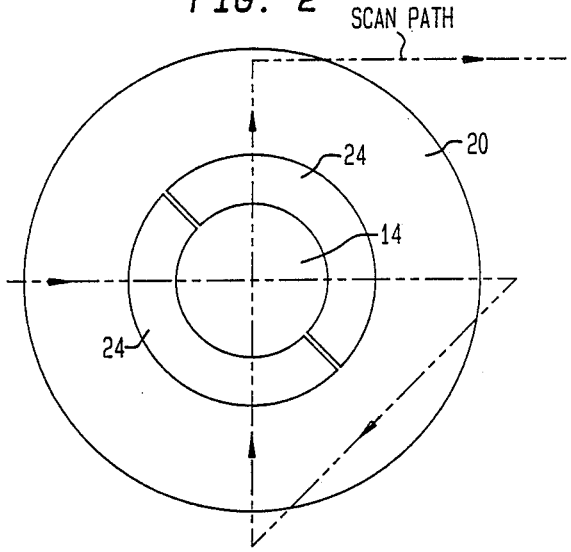
FIG. 2 is a top view of the valve spring assembly.

The sensor 12 comprises a piezo-ceramic element which resonates in response to an electrical impulse and generates a focused sound wave. The sound wave strikes a reflecting surface and returns to the piezo-ceramic element which converts the returning energy to an electrical signal. The time between the trigger impulse and the detection of the return signal is the time of flight and is a measure of the distance to the surface. We prefer a stand-off distance of 50 mm to the top of the keys. The lateral resolution or spot size of the sound wave is 0.8 mm and allows small structure such as the retainer keys to be seen. The sensor 12 is carried by a robot 26 and an air slide 27 or other mechanical manipulator for respectively accurately positioning the sensor and moving it along a prescribed path parallel to the top of the stem 14 across the assembly 10 and through the stem 14 to make measurements at hundreds of points of the distance between the sensor and the top surfaces of the stem 14, keys 24 and the cap 20. Two transverse scans at least 45 degrees apart are made on each assembly 10 to insure that a key, if present, will be detected even though the sensor might, on one scan, traverse along a gap between the keys. FIG. 2 shows the top view of the valve spring assembly 10 and a typical scan path.

Figure 3:
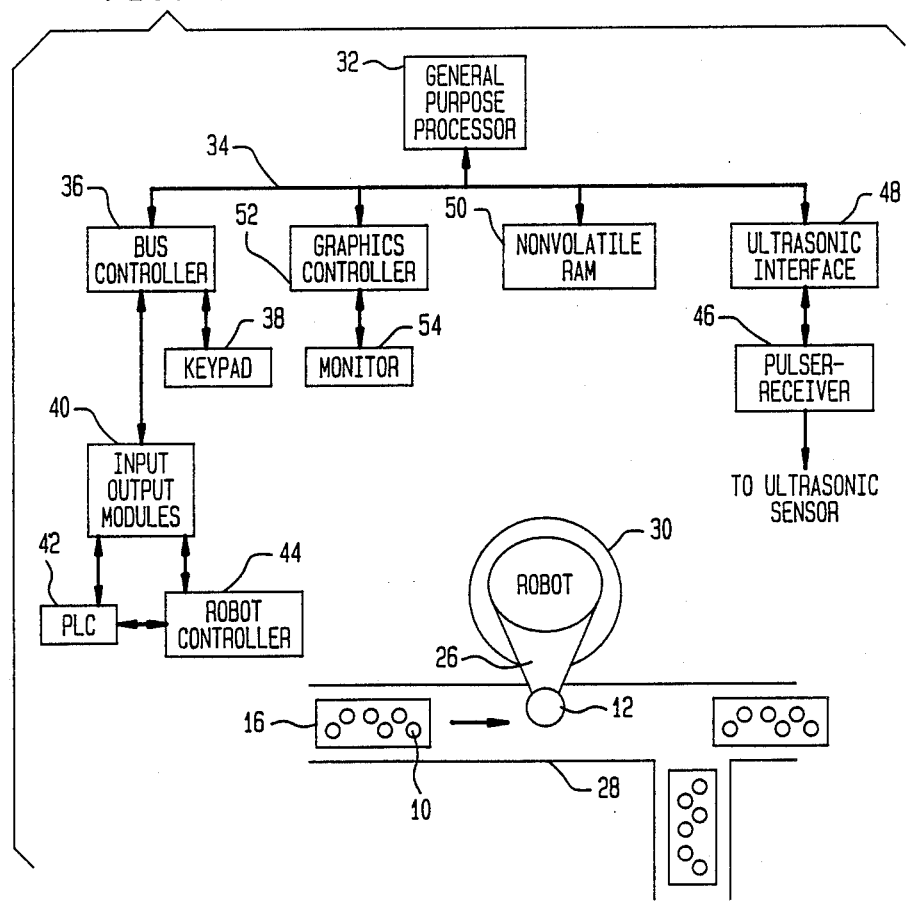
FIG. 3 is a schematic diagram of ultrasonic inspection apparatus according to the invention.

FIG. 3 is a schematic diagram of the apparatus for making the ultrasonic measurements. Engine heads 16 are moved on conveyors 28 to an inspection station where the heads are precisely located with respect to the sensor 12. The conveyor continues, after inspection, to carry the head to a repair station if a fault was found or to the next stage of production if there is no fault. A robot 30 or other manipulator controls the sensor movement. A computer or general purpose processor 32 is coupled through a bus 34 to a bus controller 36 which has a keypad 38 input. The controller 36 is connected through input/output modules 40 to a programmable logic controller (PLC) 42 and to a robot controller 44 which determines the robot movements. The sensor 12 is electrically coupled to a pulser-receiver 46 which is connected through an ultrasonic interface 48 to the processor 32.

The general purpose processor 32 is also connected to a non-volatile RAM 50 and to a graphics controller 52 and a monitor 54. The general purpose processor 32 via the input/output modules 40 coordinates the sensor movement with the taking of data and further analyzes the data to determine improper assembly. Inspection results are reported to the PLC 42 which controls transfer of heads which failed inspection to the repair line. The ultrasonic interface 48 continuously triggers the sensor through the pulser/receiver 46. When a head is transferred into the inspection station and the PLC 42 commands the robot to commence scanning, the robot controller signals the processor 32 that the robot is approaching a valve assembly and the processor 32 transfers the echoes from the interface 48 into its own memory until the scan is complete. The process is repeated for each scan of each valve.

After storage of the last scan, the processor 32 begins processing echo data. A scan consists of 1024 time of flight measurements clocked at 6 MHz. A flat or continuous surface such as the top of a valve stem, cap, or key is characterized as a series of continuous times of flight. Sharp discontinuities indicate the beginning or end of a physical feature of the assembly. The processor 32 processes the times of flight and builds a database of feature tables. Each feature is represented by a group of data points stored in memory and representing about the same time of flight. The feature table lists the beginning and ending addresses for each feature so that the size or scan distance across an element can be determined from the addresses.

An operator uses the capabilities of the teach mode to adjust inspection parameters and program constants. Inspection parameters are programmed by scanning a good valve spring assembly and defining tolerance bands or windows around the stem, cap and keys. The offsets between the stem and key windows and between the stem and cap windows are also entered. Some program constants control formation of feature tables. Examples of such constants are: minimum size of each feature, and allowable discontinuity within a feature. Others are used to establish and update a running average time of flight for all stems on valve assemblies that pass. The historical stem average is used to automatically adjust the stem window for gradual changes in ambient air temperature. Adjusting the stem window allows the method to reduce errors due to variations in the speed of sound without direct temperature sensing. Program constants and inspection parameters are stored in non-volatile memory for subsequent use in run mode.

Figure 4:
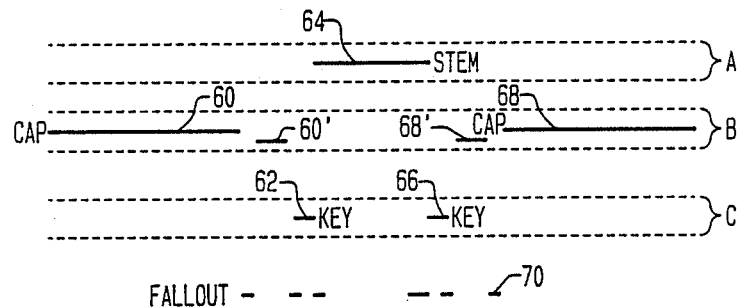
FIG. 4 is a plot of a valve spring assembly profile as determined by the apparatus of FIG. 3.

The scan of a good valve spring assembly is represented in FIG. 4 which is a plot of times of flight with the windows for the stem, cap and the keys indicated by dashed lines. From left to right the traces represent a cap 60, a key 62, a stem 64, a key 66, and a cap 68. Window A is the stem time of flight window, window B is the cap window and window C is the Key window. The cap has an inner lip which shows as an offset part 60′, 68′ of the cap feature. Lines 70 below the key windows indicate "fallout" or regions where no signal was received and result from spaces between the elements. These spaces can be used to determine the edges of features. Thus a contiguous group of data points bounded by fallout spaces is considered to be a single feature. In addition, large time of flight differences between adjacent data points can be used as the boundary indicia.

The historical average time of flight for the last twenty or thirty valves is calculated and used for the stem inspection. In the case where the various stems in a head are oriented at different angles and the stem heights are normally not the same, the historical average is calculated separately for each valve position, i.e., all number one valve stems are averaged, all number two valve stems are averaged, etc. The stem window is determined as the preset window size centered at the historical average. The database of feature tables preserves the sampling order. The search for the stem begins with the feature roughly in the middle of the scan. The feature distance (average time of flight for the points sampled for that one feature) is compared to the stem window and the feature size is compared to the model stem size. If there is no match, another feature is tried. If no match is found the stem is not in place and the assembly fails inspection. If a match is found, the key and cap windows are calculated based on the preset offsets and window sizes and the average measured time of flight for the particular stem.

Keys are expected to be the features adjacent to the stem. The presence of features with appropriate times of flight and number of echoes are denoted as good keys. The absence of features with times of flight within the window indicates a missing or high key. That is, if the feature next to the stem is outside the window and larger than the "maximum key length" parameter, the feature next to the stem is the cap. This indicates a missing key. A high key can be detected because the feature next to the stem is outside the key window and within the key size parameters.

Figure 5:
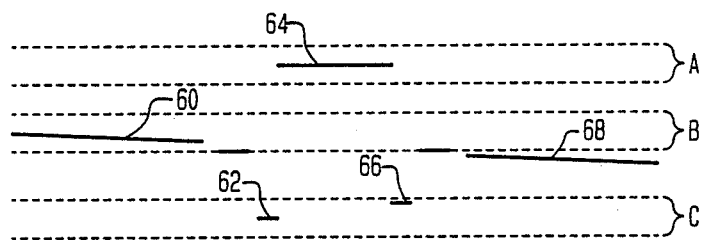
FIG. 5 is a plot of a valve spring assembly profile revealing a, high key as determined by the apparatus of FIG. 3.

Key window inspection is not sufficient to detect all high keys. Slightly high keys which, because of stackup, fall in the key window are possible. FIG. 5 depicts a profile with a slightly high key 66. To detect these keys, several inspections are performed. First, on scans where two keys are present, the minimum times of flight (tops) of the two keys are compared. A difference exceeding a parameter, "key height difference", indicates that, while both keys are within the window, only one key is correctly positioned in the stem groove.

In addition to the key height comparison, cap inspections are needed to detect some high keys. A slightly high key will cause the cap to tilt and two high keys will force the cap downward. Therefore, the cap position and slope are verified. The average time of flight for the cap must be located in the cap window. If not, a "bad key" is present. In addition to having proper height, the cap must be level. The average time of flight values for the right and left side of the cap are compared. These values must be within the cap variation limit to pass. Otherwise a "bad key" is indicated.

As a result of these inspections, various flags are set. After both scans have been inspected, these flags are used to accept or reject valve assemblies. For a good valve, a stem must be present in both scans. Otherwise the inspection result indicates a "bad stem." Each scan must contain two cap features, both within the cap window, and each scan must reveal a level cap. The key inspection results require that a good key be within the key window and that two good keys must be found in one of the scans.

Another feature extraction technique is preferably employed in an engine where the valve spring assembly, when properly assembled, has the keys and cap at the same height and has no spaces between the elements. Thus no fallout and no feature offset are present to distinguish the keys and cap. For this case, time is used to determine which data represents a particular feature. To afford consistency of scanning time of like features (and therefore the same apparent size), repeatability of scan velocity during the data acquisition is necessary and constant scan velocity is preferred.

Figure 6:
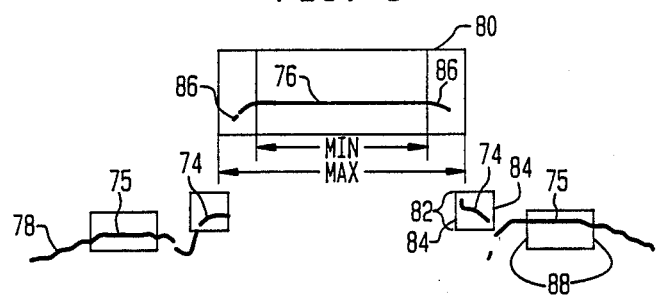
FIG. 6 is a plot of a profile of a second type of valve assembly and superimposed windows as determined by the apparatus of FIG. 3.

The profile of the assembly has contiguous key and cap feature traces 74 and 75, respectively, as shown in FIG. 6, and an elevated stem feature trace 76, assuming a proper assembly. The cap has a sloped outboard portion which yields a sloped trace 78. To analyze the trace, the historical stem average and a stem window 80 are established as in the method described above. Then the data is searched to find points in the stem window 80 and the length of that feature is compared to allowed maximum and minimum stem limits. If a key is high it may be in the stem window and add to the stem size so that the apparent stem feature size is too large and a reject flag is set. If the proper stem feature size is found in the window, the feature is accepted as a stem and windows referenced to the stem are set for the keys and cap. The latter windows are two dimensional and are conservatively chosen to assure that the space in a given window covers only a region of the respective key or cap. The key and cap offset is determined as a given distance from the measured position of the stem feature, and the associated vertical window 82 size is set by a programmed parameter. The lateral window boundaries 84 are measured as set distances from the ends 86 of the stem trace. The cap window boundaries 88 are set in the same manner. Since the traces are formed by data points which occur at clocked intervals, the lateral distances shown in the trace are actually times. Thus the period of the sensor scan is partitioned into time regions by the boundaries 84 and 88 where at least part of the key or cap is expected to be, the partitioning being measured from either end of the located stem feature. The verification of proper assembly is then done by determining that each window has the appropriate number of data points. For example, a key window lacking a set minimum number of data points would be interpreted as a missing or high key.

The embodiments of the invention in which an exclusive property or privilege is claimed are defined as follows:

1. In an ultrasonic sensing system having a sensor for inspecting a series of objects each having a plurality of surfaces facing the sensor including a reference surface at a known nominal distance from the sensor, the method comprising the steps of:
   scanning the sensor over the surfaces of the objects and recording the time of flight of the ultrasonic signals;
   determining the average time of flight to the reference surfaces in the course of inspecting a series of objects;
   for each object, establishing parameters on the desired distance of each surface from the reference surface, extracting features from the recorded time of flight data, locating the feature corresponding to the reference surface based on the average time of flight, and determining the reference time of flight;
   setting a window in which each acceptable surface other than the reference surface is to be found; and
   determining whether each feature for a respective surface is in a corresponding window.

2. The invention as defined in claim 1 including setting each window location based on the desired distance of each surface from the plane of reference surface and the reference time of flight.

3. The invention as defined in claim 2 including setting a window width corresponding to the allowable tolerance of the feature position and setting lateral window depending on feature size and position as measured from the reference surface feature.

4. The invention as defined in claim 1 including the steps of setting a reference time window around the average time of flight in which an acceptable reference surface is to be found, and determining for each object whether its reference surface is within the reference window.

5. The invention as defined in claim 1 wherein the step of establishing parameters comprises: scanning a model object with the sensor and determining an offset and a window width for each feature surface.

6. The invention as defined in claim 1 wherein the step of scanning with the sensor comprises sweeping paths along the surfaces at a repeatable rate and with ultrasonic pulses emitted at a constant frequency.

7. The invention as defined in claim 1 wherein the step of extracting features from the time of flight data comprises grouping the time of flight data for each feature distinguished from adjacent features by gaps in received data and by substantial differences in time of flight.

8. In an ultrasonic sensing system having a sensor for inspecting a series of valve spring assemblies each having a plurality of surfaces facing the sensor including keys and caps and including a stem surface at a known nominal distance from the sensor, the method comprising the steps of:
establishing desired parameters including the desired offset of each key and cap surface from the stem surface and the size of each key and cap surface;
scanning the sensor over the valve spring assemblies including the stem surfaces and recording the time of flight of each ultrasonic signal;
averaging the time of flight of the signals for a plurality of stem surfaces;
setting a time window in which a stem is to be found, the stem window being based on the allowable tolerance of the stem surface and the averaged time of flight;
for each particular stem, measuring the average time of flight for the surface and determining whether the stem surface is within the stem window;
setting time windows in which each acceptable key and cap is to be found, each window being based on the desired offset of each key and cap, respectively, and the averaged time of flight for the respective stem surface; and
determining whether the resulting time of flight for each key and cap surface is in a corresponding time window.

9. The invention as defined in claim 8 wherein an established desired parameter is that the cap be parallel to the stem surface and including the step of determining whether the cap is parallel to the stem surface by calculating the slope of cap time of flight data.

10. The invention as defined in claim 8 wherein the step of determining whether the resulting time of flight for each key and cap surface is in a corresponding time window comprises the steps of:
determining the size of each surface from the number of signal pulses at a given position; and
identifying the cap and the keys from the position and size data.

11. The invention as defined in claim 10 wherein a stream of data is generated during each scan across the assembly, and wherein the step of identifying the stem, cap and the keys comprises: searching for stem data in the center of the stream data produced during the scan across the valve assembly, verifying the position of the stem, searching adjacent the stem data for key data, and searching adjacent the key data for the cap data.

12. The invention as defined in claim 8 wherein time windows for the keys and caps are two dimensional having lateral boundaries, and the step of setting time windows further comprises: setting boundaries spaced laterally from the stem position based on the sizes and the expected distances from the stem of keys and caps respectively.

13. Apparatus for ultrasonic inspection of object configurations where each object has a reference surface and feature surfaces to be measured, comprising:
ultrasonic sensor means for emitting a series of pulses toward a surface to be measured, receiving reflected pulses and measuring the time of flight of the pulses,
means for scanning the sensor means across the object in a predetermined path along the surfaces to be measured,
memory means for storing the size of each surface along the scan path and the desired offset distance of each feature surface from the reference surface, and
computer means including the memory means for
(a) determining a reference time of flight based on a running average of pulses to the reference surfaces,
(b) setting a time window based on the reference time of flight for an acceptable reference surface,
(c) locating the reference surface within the said time window,
(d) setting a time window for each feature surface referenced to the time of flight for the located reference, and
(e) comparing the time of flight for each measured object surface to the corresponding feature time window to determine acceptability.

14. Apparatus for ultrasonic inspection of a valve spring assembly where each assembly has a reference stem surface and key surfaces to be measured, comprising:
ultrasonic sensor means for emitting a series of pulses toward the assembly to be measured, receiving reflected pulses and measuring the time of flight of the pulses,
manipulator means for scanning the sensor means across the valve spring assemblies in a predetermined path along the surfaces to be measured,
memory means for storing the size of each stem and key surface along the scan path and the desired offset distance of each key surface from the stem surface, and
computer means including the memory means for
(a) determining a reference time of flight based on a running average of pulses to a plurality of the stem surfaces,
(b) setting a time window based on the reference time of flight for an acceptable stem height, (c) locating the stem surface within the said time window,
(d) setting a key time window for key surfaces referenced to the time of flight for the located stem surface, and
(e) comparing the time of flight for each measured key surface to the corresponding key time window to determine acceptability.

15. Apparatus for ultrasonic inspection of a valve spring assembly where each assembly has a reference stem surface and key and cap surfaces to be measured, comprising:

ultrasonic sensor means for emitting a series of pulses toward the assembly to be measured, receiving reflected pulses and measuring the time of flight of the pulses, manipulator means for scanning the sensor means across the valve spring assemblies in a predetermined path along the surfaces to be measured, memory means for storing the size of each stem, key and cap surface along the scan path and the desired offset distance of each key surface from the stem surface, and computer means including the memory means for
(a) determining a reference time of flight based on a running average of pulses to a plurality of the stem surfaces,
(b) setting a time window based on the reference time of flight for an acceptable stem height,
(c) locating the stem surface within the said time window,
(d) setting cap and key time window for cap and key surfaces referenced to the time of flight for the located stem surface,
(e) comparing the time of flight for each measured key surface to the corresponding key time window,
(f) determining cap tilt from the measured cap surfaces, and
(g) determining acceptability from the presence of key surfaces within the key windows and from the cap tilt.

* * * * *